(12) United States Patent
Lalonde et al.

(10) Patent No.: US 6,283,959 B1
(45) Date of Patent: Sep. 4, 2001

(54) ENDOVASCULAR CRYOTREATMENT CATHETER

(75) Inventors: Jean Pierre Lalonde, Verdun; Robert Martin, St. Laurent; Claudia Lueckge, Pierrefonds; Leonilda Capuano, Montreal, all of (CA); John W. Lehmann, Wayland, MA (US); Daniel Nahon, Ottawa (CA)

(73) Assignee: CyroCath Technologies, Inc., Kirkland (CA)

( * ) Notice: Subject to any disclaimer, the term of this patent is extended or adjusted under 35 U.S.C. 154(b) by 0 days.

(21) Appl. No.: 09/378,972

(22) Filed: Aug. 23, 1999

(51) Int. Cl.[7] ..................................................... A61B 18/18
(52) U.S. Cl. .................................. 606/21; 606/23; 606/24
(58) Field of Search ................ 128/DIG. 27; 606/20–27; 607/105

(56) References Cited

U.S. PATENT DOCUMENTS

| | | | |
|---|---|---|---|
| 5,246,421 | 9/1993 | Saab | 604/96 |
| 5,273,526 | 12/1993 | Dance et al. | 604/35 |
| 5,484,385 | 1/1996 | Rishton | 600/16 |
| 5,632,762 | 5/1997 | Myler | 606/194 |
| 5,725,521 | 3/1998 | Mueller | 606/7 |
| 5,776,129 | 7/1998 | Mersch | 606/31 |
| 5,827,273 | 10/1998 | Edwards | 606/41 |
| 5,860,971 | * 1/1999 | Clarke | 606/24 |
| 5,868,735 | * 2/1999 | Lafontaine | 606/21 |
| 5,899,899 | * 5/1999 | Arless et al. | 606/22 |
| 5,902,299 | * 5/1999 | Jayaraman | 606/20 |
| 5,971,979 | * 10/1999 | Joye et al. | 606/21 |
| 6,106,518 | * 8/2000 | Wittenberger et al. | 606/23 |

FOREIGN PATENT DOCUMENTS

WO 9927862 6/1999 (WO) ............................ A61B/17/36

* cited by examiner

Primary Examiner—Linda C. M. Dvorak
Assistant Examiner—David M. Ruddy
(74) Attorney, Agent, or Firm—Gunster, Yoakley & Stewart, P.A.

(57) ABSTRACT

A catheter is attached to an elongated catheter body adapted for endovascular insertion with a balloon assembly at its distal end. Coolant injected through the catheter body may, in different embodiments, directly cool tissue contacting the balloon, or may cool a separate internal chamber. In the first case, the coolant also inflates the balloon, and spent coolant is returned to the handle via a return passage extending through the body of the catheter. A valve may regulate back pressure in the return passage to coordinate the flow of coolant into and out of the balloon so as to both inflate the balloon and achieve cryogenic cooling at the surface of the balloon. The coolant is biologically safe, and may be liquid carbon dioxide. Plural balloons may be provided adjacent the cooling segment, and one balloon may be shaped to treat the ostium of a vessel. Preferably, thermal conductivity of the balloon wall is enhanced by inclusion of thermally conductive material, such as metal, which may be introduced as a component of a composite elastomer material, or as a patterned metal layer that defines a pattern of thermally conductive treatment regions of the balloon surface. Patterns formed by printing, lithography or other means with copper, silver or other highly thermally conductive material enhance through-conduction characteristics of the wall so icing preferentially occurs to stimulate tissue destruction and vascular regeneration. Suitable patterns include spirals, dots, arrays of separated segments, or meandering curves which allow expansion of the balloon body without introducing delamination, localized stress cracking or separation of the balloon material. The conductive patterns may include patterns such as waffle-iron or other arrays of small lesions that are effective to treat the endovascular wall. When separate media are used for cooling and for balloon expansion, the cooling chamber may have a large diameter, and the balloon may form a thin shell or cuff. In that case, the balloon may be quickly inflated with a medium such as a saline to provide a quickly deployed and compliant contact structure of excellent conductivity.

17 Claims, 6 Drawing Sheets

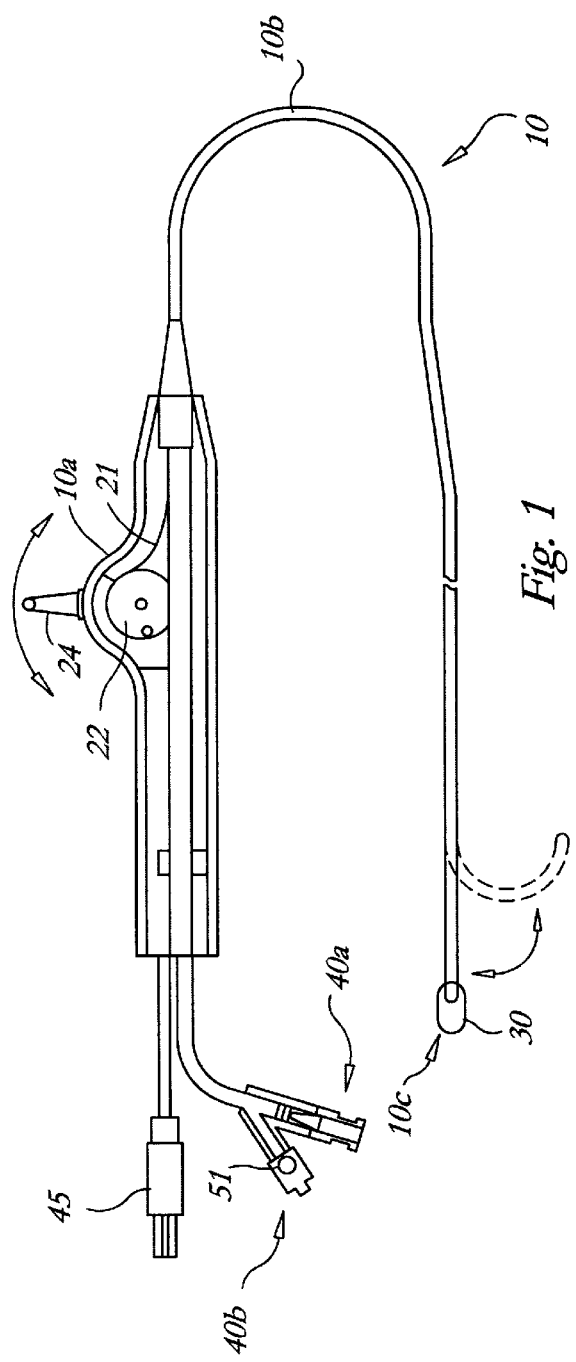
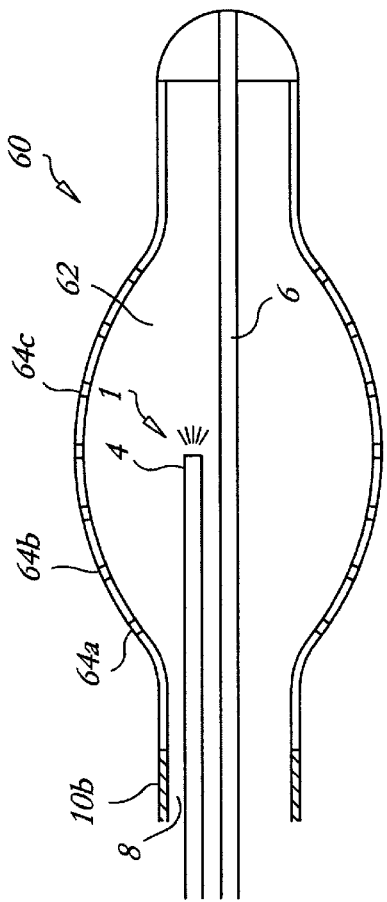
Fig. 1
Fig. 2

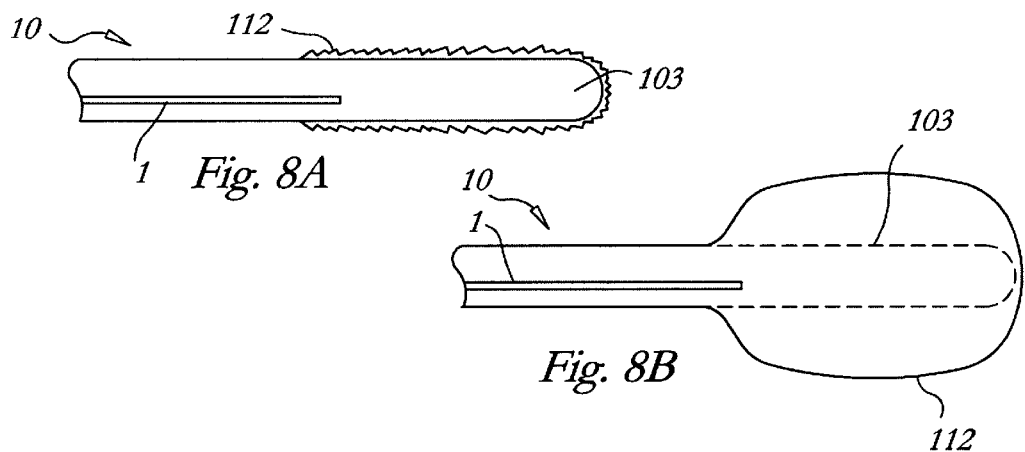
Fig. 8A
Fig. 8B
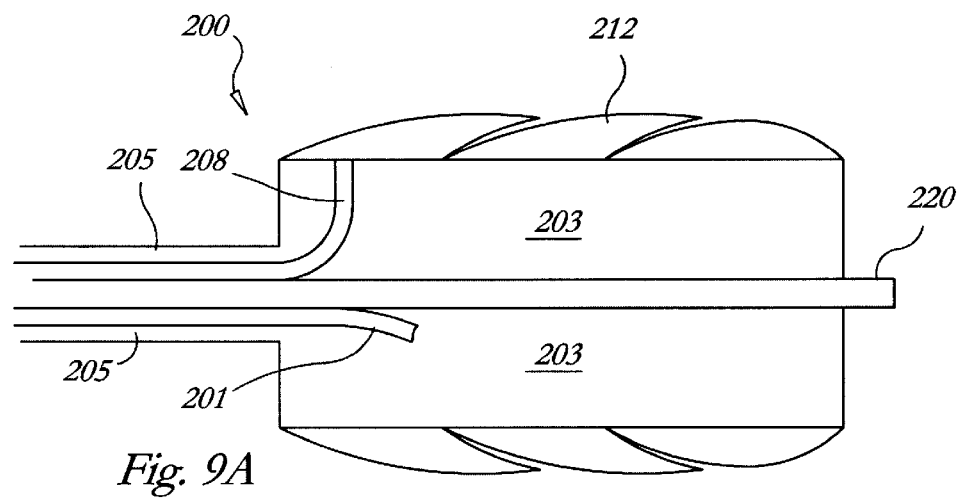
Fig. 9A
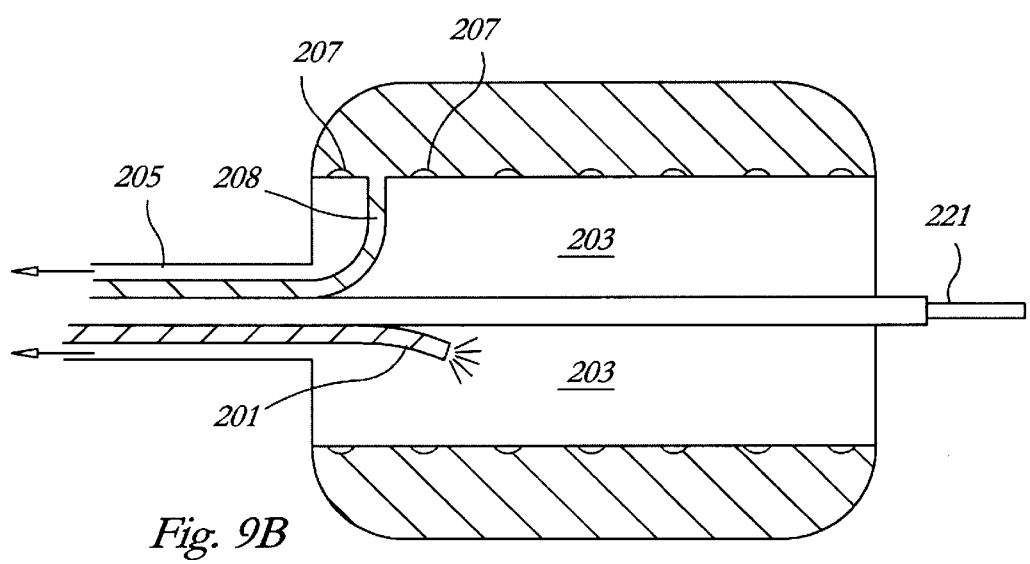
Fig. 9B

ENDOVASCULAR CRYOTREATMENT CATHETER

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates to endovascular cryocatheters, such as angioplasty balloons having a freezing function for treating tissue by extreme cooling contact. These catheters have an elongated body through which a cooling fluid circulates to a tip portion which is adapted to contact and cool tissue. Such a device may include a steering assembly such as an inextensible pull wire and a flexible tip to which the pull wire attaches which may be bent into a curved configuration to aid its navigation through blood vessels to a desired treatment site. When used for angioplasty or the destruction of tissue on the inner wall of a vessel, the catheter generally also has one or more inflatable balloon portions which may serve two functions of displacing blood from the treatment site to allow more effective cooling, and physically distending the affected vessel to break up accumulations of plaque.

Endovascular catheters must be of relatively small diameter, and configured for insertion along relatively confined pathways to reach an intended ablation site. As such, the cooling fluid must circulate through a relatively long and thin body yet apply significant cooling power in their distal tip. The requirement that coolant be localized in its activity poses constraints on a working device. For example, when the catheter must chill tissue to below freezing, the coolant itself must obtain a lower temperature to offset the conductive warming effects of adjacent regions of body tissue. Furthermore, the rate of cooling is limited by the ability to circulate a sufficient mass flow of coolant through the active contact region. Since it is a matter of some concern that proximal, adjacent or unintended tissue sites should not be exposed to harmful cryogenic conditions the flowing coolant must be exposed in a limited region. One approach to cooling uses a phase change refrigerant which is provided through the body of the catheter at relatively normal or ambient temperature and attains cooling only upon expansion within the tip region. One such device treats or achieves a relatively high rate of heat transfer by using a phase change coolant which is pumped as a high pressure liquid to the tip of the catheter and undergoes its phase change expanding to a gas in a small chamber located at the tip. The wall of the chamber contacts the adjacent tissue directly to effect conductive cooling or ablation treatment. Other cryocatheters may employ gas at high pressure, and achieve cooling via the Joule-Thomson effect at a spray nozzle in a cooling chamber at the distal end of the catheter.

In an endovascular catheter as described above, a relatively high cooling power may be obtained. However, the expansion of a phase change or high pressure coolant exiting from a nozzle within a small catheter tip creates highly turbulent flow conditions. The cooling region of the tip may be implemented as a fairly rigid chamber having highly thermally conductive wall or section of its wall formed for example by a metal shell. However, if one were to replace such a tip with an inflatable balloon as is commonly used for angioplasty, the size of the chamber would vary considerably as the balloon is inflated, causing substantial variations in flow conditions of the fluid entering the tip and substantial changes in heat transport across the expanding balloon wall. Both of these factors would result in variations of the cooling power over the tip. Furthermore, coolant materials suitable for high pressure or phase change refrigeration may pose risks when used within a blood vessel. Accordingly, there is a need for an improved catheter construction for cryogenic angioplasty.

Another factor which adds complexity to the task of cryocatheter design is that the primary mechanism of treatment involves thermal conduction between the catheter and a targeted region of tissue. Thus, not only is the absolute cooling capacity of the catheter important, but the nature and extent of contact between the cooled region of the catheter and the adjacent tissue is important. Effective contact may require moving, positioning, anchoring and other mechanisms for positioning, stabilizing and changing the conformation of the cooled portion of the catheter. Slight changes in orientation may greatly alter the cooling range or characteristics of the catheter, so that even when the changes are predictable or measurable, it may become necessary to provide positioning mechanisms of high stability or accuracy to assure adequate treatment at the designated sites. Furthermore, it is preferable that a vessel be occluded to prevent warming by blood flow during treatment. Beyond that, one must assure that the cooling activity is effective at the surface of the catheter, and further that defects do not cause toxic release of coolant or dangerous release of pressure into the body.

Secondary environmental factors, such as the circulation of blood near or at the treatment site may also exert a large influence on the rate at which therapeutic cooling accrues in the targeted tissue.

There is therefore a need for improved cryocatheter constructions to occlude blood flow and form a dependable thermal contact with a vessel wall.

SUMMARY OF THE INVENTION

One or more of these and other desirable features are achieved in a catheter having a handle adapted to receive a supply of coolant and a return port for return of spent coolant. The handle is attached to an elongated catheter body adapted for bodily or endovascular insertion with a tip assembly at its distal end. The tip includes an inflation balloon into which the coolant is injected and from which spent coolant is returned to the handle via a return passage extending through the body of the catheter. A valve or controller regulates back pressure in the return passage to coordinate the flow of coolant into and out of the balloon so as to both inflate the balloon and achieve cryogenic cooling at the balloon wall. Preferably the coolant is liquid carbon dioxide, but in various configurations discussed further below, coolants such as saline or high pressure refrigerants may also be used.

In a preferred embodiment, thermal conductivity of the balloon wall is enhanced by inclusion of thermally conductive material, such as metallic material, which may be introduced as components of a composite elastomer material, or as a patterned metallic layer to form a pattern for thermal treatment. The metallic patterns may be formed by printing, lithography or other means, and are preferably formed of copper, silver or highly thermally conductive material so that the through-conduction characteristics of the balloon wall are enhanced in the metal regions. Suitable patterns include spirals, dots, arrays of separated segments, or meandering curves which are composed of continuous, and possibly connected regions that are shaped to allow expansion of the balloon body without localized stress cracking or separation of the balloon wall material. The applied conductive patterns form areas of enhanced thermal conductivity at which icing preferentially occurs to stimulate tissue destruction and vascular regeneration. Thus, patterns are preferably ones such as waffle-iron or arrays of small lesions that are effective to treat the endovascular wall. The back pressure in the return line may be provided by a check valve release, which, moreover, may vent directly to the atmosphere when a coolant such as liquid carbon dioxide is used. The valve is preferably configured to maintain, during inflation, a pressure differential between the injection and the release, or a back pressure in the return line, which may for example be on the order of ten psid or more, sufficient to maintain adequate cooling circulation through the catheter while inflating the balloon.

In accordance with another aspect of the invention, there is provided a cryocatheter having a balloon assembly at its cooling end in which a first balloon inflates to anchor a flexible but non-expanding cooling segment and a second balloon is spaced from the first balloon by the cooling segment. The segment may, for example, include a metal wrapped portion of the catheter body between the two balloons. In one embodiment of this aspect of the invention, the second balloon is a tapered balloon, such as a trumpet-shaped or bell-shaped balloon, configured to lodge in the ostium and occlude blood flow while positioning the cooling segment. The first balloon may be an anchor balloon, and this balloon may have a separate inflation lumen, allowing it to inflate first to set the initial position of the distal catheter end. As with the first embodiment described above, cooling is preferably accomplished using liquid carbon dioxide or other suitable biocompatible liquid, and the coolant return passage may be operated with a positive coolant back pressure serving to inflate and maintain inflated one or more of the balloons. The balloon positions may be inverted for use in either antegrade or retrograde treatment approaches and additional lumens may be provided to inflate each balloon independently, or inflate the anchor balloon independently of cooling system operation.

In accordance with yet another aspect of the present invention, a body insertable cryotreatment balloon assembly is configured with a distal cooling tip assembly having a cooling chamber surrounded by an expansion balloon. The cooling chamber is of small diameter and is substantially rigid or non-expanding, and may be cooled with high efficiency by a phase-change refrigerant, while the balloon surrounds the chamber and is inflated by a liquid such as saline aqueous solution having a relatively high thermal conductivity and heat capacity, and, incidentally, being substantially incompressible. The cooling chamber may be thus configured to optimize the applied cooling power, in regard to the flow of coolant through the catheter, while the balloon which forms a sleeve around the chamber provides significant improvements in compliance degree and area of tissue contact, heat transfer, and safety and control of the expansion characteristics. The inflation sleeve may extend beyond the cooling chamber to form uncooled cushions or cuffs that operate to occlude flow or isolate the central cooling portion from blood or body fluids, thus further augmenting the achievable rate of cooling. In yet other embodiments, the shape of the balloon may be used for end-occlusion around the cooling segment to control the general contours of the ice ball which forms at the cooling chamber region. In a still further embodiment the cooling chamber and surrounding balloon may be configured with one or more through-flow or relief passages to allow continued circulation of blood along the lumenal path before, during or after the balloon inflation and cooling of the lumenal wall. In general, the constructions of the present invention are of broad generality, and in addition to applications to endovascular cryocatheters, they may be applied to cooling other cylindrical tissue structures or body lumens, including organs or structures such as the fallopian tube, esophagus, biliary duct, ureter, gastrointestinal tract and the bronchus. For each of these different applications, the relative diameter of the cooling chamber wall, thickness of a balloon portion and other components may be varied so as to achieve, for example, a high total amount of cooling with a large cooling chamber, and an effective transfer of heat from the surrounding tissue area through a relatively thin conduction assembly or wall. Notably, the balloon embodiments may be inflated with a medium such as a precooled saline solution having a high rate of thermal conductivity and a high thermal storage capacity.

BRIEF DESCRIPTION OF THE DRAWINGS

The invention will be more fully understood from the following detailed description taken in conjunction with the accompanying drawings of illustrative embodiments, in which:

FIG. 1 illustrates a balloon catheter system in accordance with a first embodiment of one aspect of the present invention;

FIG. 2 shows a cross section taken along the axial direction through the balloon portion of another embodiment of the invention;

FIGS. 8A and 8B show another balloon embodiment of the invention in its deflated and inflated state, respectively;

FIGS. 9A and 9B show a balloon embodiment with separate cooling and inflation media;

DETAILED DESCRIPTION

Figure 3A:
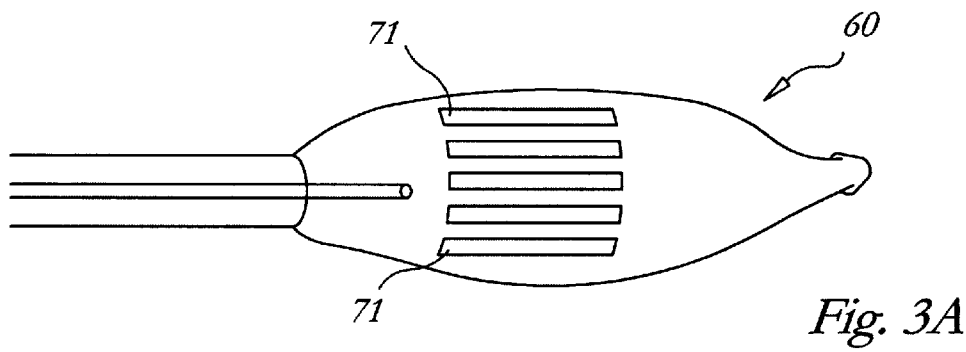
FIGS. 3A–3D illustrate four embodiments of thermally conductive balloons in accordance with the invention.

FIG. 1 illustrates a treatment catheter 10 in accordance with a basic embodiment of the present invention. Catheter 10 includes a handle 10a, an elongated intermediate body portion 10b, and a distal end 10c. An inextensible guide wire 21 extends from the handle to the tip 10c for exerting tension via a take up wheel 22 that is turned by lever 24 to curve the tip of the catheter and steer it through various branch points along the route through a vessel to the intended treatment site. Alternatively, the catheter may be provided with a central guide wire lumen. In that case, a guide wire is inserted into the vessel up to or past the treatment site and the catheter is then placed over the guide wire. As further shown in FIG. 1, a balloon 30 is attached to the distal end of the catheter and as described further below is in communication via the intermediate body 10b and handle 10a with an inlet 40a for the refrigerant fluid, and an outlet 40b through which spent refrigerant returns. The handle may also receive electrical connections via a port or cable 45 for various sensing or control functions described further below.

General principals concerning the construction or operation of such a cryocatheter may be found in U.S. Pat. No. 5,281,215 and in the descriptive material appearing on the web site www.cryocath.com, all hereby incorporated herein by reference for purposes of disclosure and illustration.

In accordance with one aspect of the present invention, the refrigerant fluid applied at the port 40a is applied through a first passage to the balloon and returned from the balloon through a second passage to the outlet 40b, at a positive pressure. For example, a valve may be present downstream of the balloon to set a back pressure which effects inflation of the balloon by the coolant fluid. As illustrated in FIG. 1, the valve may be implemented by a check valve 51 positioned at the port 40b and set for example to open at a pressure of 10 psig to maintain a sufficient back pressure in the return line for inflation of the balloon 30. In alternative embodiments, the check valve 51 may be replaced by a controllable valve, or a pressure sensing arrangement that provides a feedback signal in conjunction with an electrically controlled valve, to assure that the desired inflation pressure is achieved at the balloon 30 while allowing return of coolant continuously through the outlet 40b to a control console. In either case, the return valve maintains a minimum pressure at the outlet side of the catheter assembly. This minimum pressure is at a level higher than blood pressure to assure that the balloon inflates and occludes the vessel in which it is located.

In one embodiment, a relatively thin balloon is placed at the end of the catheter and is folded over the shaft so that when the coolant fluid is injected, the balloon opens and inflates to occlude blood flow within the vessel where it is situated. By increasing the injection pressure to the balloon, the rate of cooling is increased to apply cryogenic conditions at the surrounding wall of the vessel. Preferably, a refrigerant such as liquid $CO_2$ is employed having relatively controllable thermal characteristics for the desired treatment range. Leakage of $CO_2$ into the blood stream, if it occurs, is harmless in small amounts. This construction may be varied somewhat. For example, the balloon may be a relatively thick-walled balloon intended when inflated to exert mechanical force against the vessel wall to break up plaque. In that case, relatively higher inflation pressures are used, and the outlet valve 51 may be operated to maintain back pressures up to several atmospheres or more. Furthermore, it will be understood that the relatively small cross-sectioned opening present in the body 10d of the catheter may itself operate to cause a pressure drop, or back pressure, so that the valve 51 may be set to a lower opening pressure threshold, so long as back pressure at the balloon is maintained sufficiently high in the range for balloon inflation.

In accordance with one aspect of the present invention, the balloon operates to treat adjacent vascular tissue by freezing.

This is achieved in one preferred aspect of the invention by a balloon fabricated with a wall metallization that enhances the heat transfer rate through all or a portion or pattern of the balloon wall. FIG. 2 is a cross-sectional view through one such balloon 60 taken in a plane along the axis of the device. As shown, the balloon 60 is attached to the end of the catheter shaft 10b and has a refrigerant injection tube 4 extending to its interior so that refrigerant flows out the end or other apertures which are provided in the distal portion of the tube 4 and fills a chamber 62 defined by the interior of the balloon. A guide wire lumen 6 may extend to the distal tip for facilitating insertion, and a steering wire (not shown) may be positioned in the adjacent portion of the tip or extend through the balloon, in a manner generally known in the art of catheter design to deflect the tip portion. Within the body of the catheter shaft 10b, the region of the lumen not occupied by the injection tube and other described components serves as a return passage for the refrigerant released from the nozzle end 1 of the injection tube 4. As further shown in FIG. 2, the balloon 60 has a wall of membrane thickness with a pattern of metallization, visible as metal regions $64_a$, $64_b$ . . . $64_c$ disposed over its surface. The patterned metallization regions 64 have higher thermal conductivity than the bulk balloon membrane material, and define regions at which destructive freezing contact to the vessel wall itself will occur when the balloon is inflated.

FIGS. 3A through 3D illustrate various patterns suitable for use in the present invention in perspective view on a representative balloon 60. As shown in FIG. 3A, one such pattern includes a plurality of substantially axially oriented lines 71 disposed around the circumference of the balloon. The balloon is shown in a partially inflated posture. When inflated more fully, the balloon expands and the lines 71 move apart around the circumference. Since expansion occurs only in the radial direction, the metal does not constrain expansion of the balloon or introduce localized stresses or cracking during expansion.

Figure 3B:
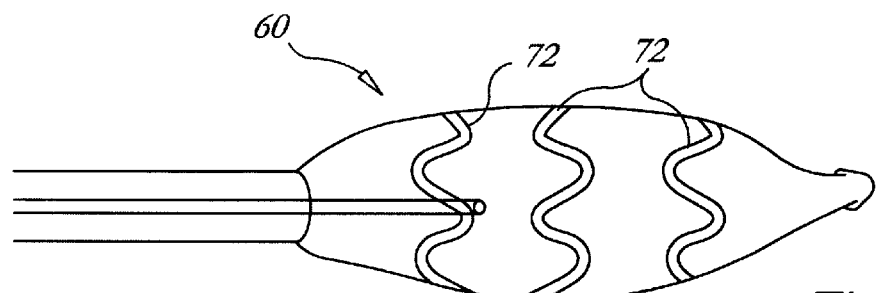

FIG. 3B shows a second useful pattern in which the conductive pattern include a zigzag or meandering arrangement of conductive metal portions 72 configured such that bends or junctions of successive path region allow the balloon to expand without constraint. In this case, radial enlargement and circumferential expansion of the balloon wall simply bends the metal paths. In general, any of the shapes which have been found suitable for expanding metal mesh, wire or coil stents may be useful as surface patterns for the balloon membrane to enable it to undergo radial expansion without introducing mechanical faults into the balloon membrane.

Figure 3C:
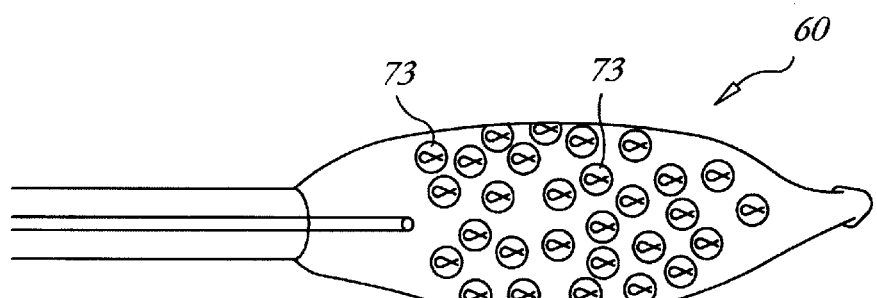

The invention also contemplates conductive patterns in which the conductive regions consist of a plurality of substantially separated or disjoint small loci. These may consist of solid regions such as dots 73, or squares or rectangles of relatively small overall extent, e.g., under several millimeters across, to produce dimpled regions of conduction extending over the whole surface of the balloon as shown in FIG. 3C, or may include one or more large areas so as to adapt the balloon for applying a particular pattern of localized cooling, such as a cooling through on side of the balloon while still allowing the balloon to expand in its entirety to firmly lodge the balloon within the vessel and displace blood so as to allow the cooling surface of the balloon to effectively and directly contact the vessel wall.

Figure 3D:
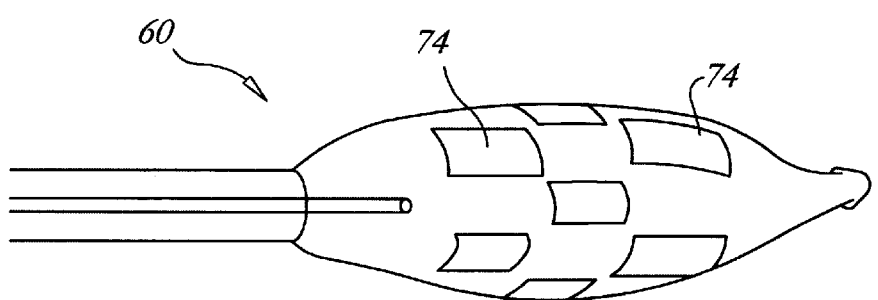

FIG. 3D shows another useful pattern 74 for the balloon.

The metal or conductive regions 71, 72, 73 and 74 may be applied using lithographic printing technology, for example, by applying a metal-loaded thermally conductive ink in a polymer base to the membrane, or by applying complete coatings and patterning and etching away regions by lithography techniques to form the desired pattern. Such patterns may also be formed by applying a metal foil layer or depositing such a layer by plating or sputter deposition techniques and employing lithographic methods to pattern the continuous layers. In general the pattern is formed so as to create a desired pattern of icing lines for effectively destroying tissue at the patterned areas of conductive contact when the balloon is inflated. The conductive regions 64, 71–74 may also be created by adding thermally conductive materials such as copper powder, flakes or fibers to the material of the balloon membrane itself. In that case the powders or fibers are preferably mixed with the appropriate elastomer or polymer material from which the balloon is to be formed, and the balloon is then formed by a known technique such as molding, forming on a mandrel, dipping or other common balloon forming technique. When patterning is desired, a standard elastomer and a conductively loaded elastomer may be painted on in bands or otherwise patterned during the manufacturing process to create the desired thermal contact regions.

Figure 4:
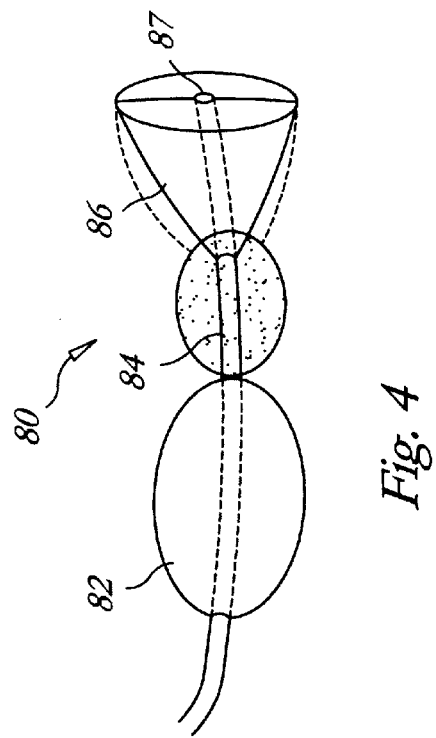
FIG. 4 illustrates another embodiment of the invention.

FIG. 4 illustrates another embodiment 80 of the present invention. This embodiment has a multi-balloon structure and a cooling segment 84 at the catheter tip. As illustrated, segment 84 corresponds to the expansion chamber or region of greatest cooling activity of the catheter and includes a cooling pattern assembly. This may be a spiral metal wrapping that provides stiffness, form and thermal conductivity to the segment. A first balloon 82 is positioned on one side of the cooling segment 84 to serve as an anchor and blood vessel occluder or flow blocker, and in this embodiment a second balloon 86 extends from the other end of the cooling segment. As shown, the first balloon is substantially ovaloid and symmetrical, while the second balloon 86 has a tapered, trumpet-or bell-shaped aspect that allows it to wedge at the end of a vessel, for example, in the ostium or junction of the vessel end to an organ. Thus, while the balloon 82 is inflatable within a vessel to serve as an anchor, balloon 86 is adaptable to fit in an opening and occlude the opening, or define an end-contact geometry for positioning the cooling segment 84 in close proximity to the vessel end opening.

It will be appreciated that the cooling segment 84 in this embodiment has a relatively fixed diameter and is not subject to inflation. Rather it has high thermal conductivity and in use when actuated by flow of refrigerant within the catheter, an ice ball forms to extend its thermal range. The region of ice formation is indicated schematically by the external dotted profile positioned around the cooling segment of the catheter.

As further shown in FIG. 4, the catheter assembly may include a guide wire lumen 87 for over-the-wire insertion, or for monorail guiding movement of the distal tip. Alternatively, the distal termination may include a conventional wiggler tip or a steering assembly manipulated from the handle end of the catheter. Furthermore, the positions of the balloons 82 and 86 may be interchanged, with the anchor balloon 82 being positioned distal to the cooling segment 84 and the tapered or trumpet balloon 86 positioned proximally thereof. This configuration allows use of the catheter by insertion along the opposite direction of the vessel, for example, through a cardiac chamber and into a vessel exiting the chamber.

Thus, in accordance with this aspect of the invention, the cryocatheter includes a cooling segment that is positioned and anchored by one or more occlusion balloons. Preferably at least one of these balloons is inflated with the carbon dioxide or other biocompatible refrigerant from the cooling segment. The balloons are not necessarily of equivalent dimension, geometry or compliance. The anchoring balloon may be inflated via an individual inflation lumen, thus allowing the position to be precisely set and this balloon inflated before cooling is initiated. The tapered balloon may be inflated in multiple ways depending on the desired effect. For example, when it is desired to treat a lesion in a vessel in close proximity to the ostium, for example, in the renal arteries, the catheter may be configured such that the coolant both inflates and cools the balloon 86, so that its tapered surface is a contact cooling surface for treating the adjacent vessel tissue.

In another embodiment, an individual inflation lumen may be provided for the flared balloon 86. In that case, this balloon may be inflated first when it is desired, for example, to place the cooling segment 84 in close proximity to the ostium. Balloon 86 may then serve the function both of positioning the cooling segment, and of occluding blood flow in the treated region. Thus, the catheter of FIG. 4 may be used for cryogenic treatment in a blood vessel and is well adapted to forming lesions near or at the ostium of the vessel. As noted above, by reversing the positions of balloons 82 and 86, the catheter may be navigated from the opposite direction along a vessel to treat a site near a junction. Furthermore, by reversing the taper orientation of the balloon 86, the catheter may be configured to more effectively treat a junction of particular size and accessible from one orientation.

Figure 5:
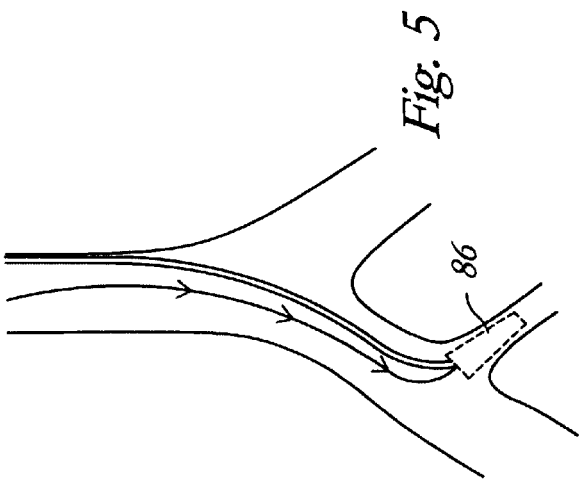
FIG. 5 illustrates balloon orientation.

In yet another embodiment, the catheter is manufactured without the symmetric anchoring balloon 82 and carries only the cooling segment 84 and trumpet balloon 86 at its tip, forming a configuration for making relatively linear lesions in locations where the vessel diameter changes rapidly. For example, such a modified catheter may be used for treatment in an antegrade approach to a treatment site along the femoral artery, as shown in FIG. 5.

Figure 6:
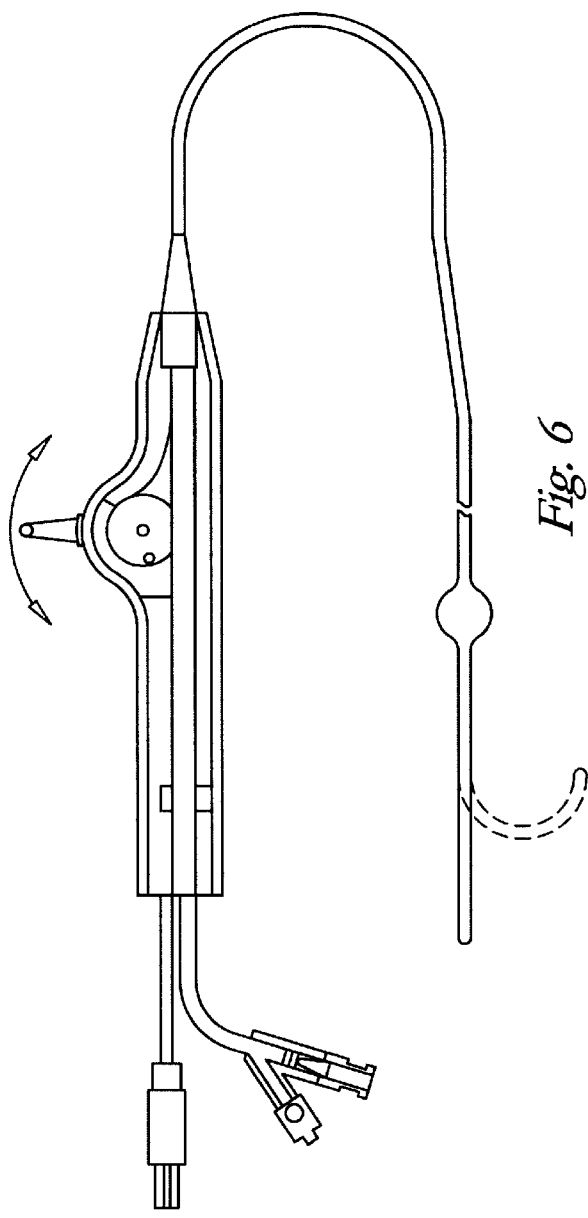
FIG. 6 illustrates an embodiment with proximal anchoring/occlusion balloon.

FIG. 6 shows another embodiment of the invention. This embodiment is similar to that of FIG. 1, but the catheter tip is configured so that rather than applying cryogenic cooling through an expandable balloon, the cooling segment is of substantially fixed diameter, which may be comparable to that of the catheter body, and it extends distally from a proximal balloon which functions to occlude the blood vessel in which the catheter lies. As shown, the tip portion is deflectable by means of a tension wire connected to the handle, so as to more effectively navigate along vascular branching passages. The tension wire may also be operated to urge the cooling segment into contact at the intended target site. As in the embodiment of FIG. 1, the coolant is preferably liquid carbon dioxide, and the coolant return line is kept at a pressure higher than the nominal blood pressure in the vessel being treated. The balloon may thus communicate with the return flow of gas so that the returning coolant inflates the balloon and effectively occludes the vessel. By placing the balloon sufficiently far downstream from the cooling segment or liquid expansion opening, the return gas may be warmed sufficiently to avoid freezing tissue in the balloon occlusion region. Similarly, by locating the balloon closer to the freezing segment, the cooler carbon dioxide will provide cryogenic treatment through the balloon surface to an additional region of tissue adjacent the cooling segment. In further embodiments, a distal balloon (not shown) may also be provided. A limiting orifice is preferably placed in the catheter lumen between the coolant injection tube and the distal balloon to prevent cold gas from entering the balloon too rapidly. Thus, the distal balloon is trickle-filled from the expansion region of the catheter to provide dependable occlusion or anchoring without damaging surrounding tissue.

In any of the foregoing embodiments, applicant contemplates that a valve release, or an actively-switched vacuum connection may be provided to quickly deflate the balloons on demand by reducing back pressure of the return lumen in the catheter body.

Figure 7A:
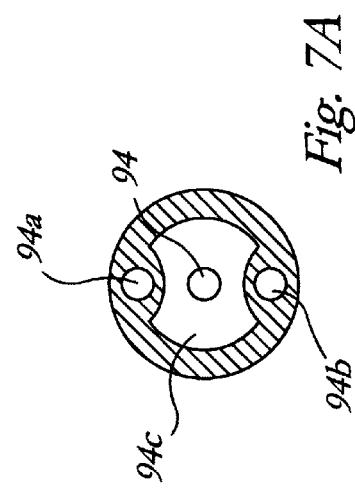
FIG. 7A illustrates a section through a multilumen catheter suitable for the practice of the invention.
Figure 7:
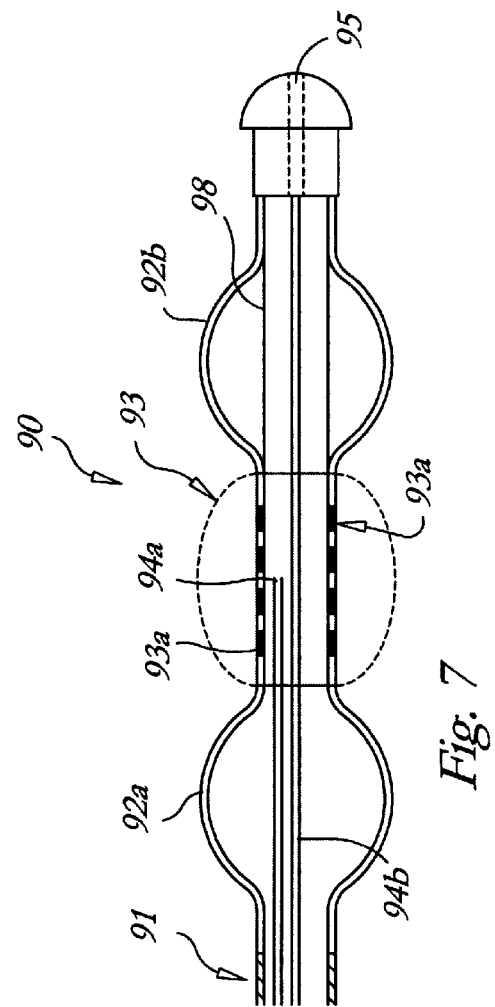
FIG. 7 illustrates another two balloon cryocatheter.

FIG. 7 shows another embodiment 90 of the invention, illustrated by way of an axial cross-section taken in a diametral plane through the tip of the catheter. As shown, the tip of the catheter comprises a pair of balloons 92a, 92b surrounding a cooling segment 93. As shown, the cooling segment and balloons may be formed by a common cylindrical membrane surrounding the catheter body, while the elongated catheter body provides necessary lead in and return passages for inflation of the balloons and delivery of cooling fluid. The cooling segment possesses a heat exchanging surface 93a which may also be a metallic or structural component of the device. For example, the surface indicated by elements 93a in the Figure may be formed by a metal spring surrounding the body, or by a metal coating or foil lithographically etched to form a coil embedded in or surrounding the membrane. Alternatively, or in addition, the cooling segment may be implemented by a helically slotted coolant supply tube fixed in the lumen of the catheter shaft to preferentially direct the coolant in liquid form against the wall of the coolant segment. In this embodiment, the catheter shaft 91 is preferably a multilumen shaft, implemented as shown, for example, in FIG. 7A. The lumena may include, in addition to a guide wire lumen if one is provided, a lumen 94 for coolant delivery, a larger return lumen 94c which may surround the delivery lumen, and one or more auxiliary lumens 94a, 94b. In various embodiments the auxiliary lumens are connected via the handle to separately inflate one or more of the balloons 92a, 92b. Alternatively, when balloon inflation is performed by trickle inflation of gas from the cooling segment 93, an auxiliary lumen may be used for a controllable vacuum passage which is actuated to deflate a balloon. As noted above, inflation of the balloons may be effected by the spent or warmed phase change coolant gas in its course towards the return lumen.

When balloon inflation is entirely effected by gas from the cooling segment, one or more of the lumena may be used to contain a steering wire or other accessory unrelated to fluid transfer. Thus as illustrated in FIG. 7, the catheter 90 may be configured with a guide wire lumen 95 for navigation within a vessel, or may include a steering and support wire assembly 98 within the catheter body to aid insertion. The invention also contemplates that, in a manner similar to the embodiments described above, the catheter 90 may be implemented with a single occlusion balloon, which is preferably placed proximal to the cooling segment for antegrade approaches to lesion treatment. Alternatively, the balloon may be placed distally of the cooling segment when it is desired use the device for treating lesions by a retrograde approach. When both occlusion balloons 92a, 92b are present, the cooling segment is readily anchored in short, branched or turning passages by inflating one or both balloons. The balloons may further be of different sizes or may be shaped as discussed above for particular applications and vessels.

In addition to the specific embodiments discussed above, in one aspect of the present invention, the invention include a balloon disposed as an annular chamber or cuff around a cooling assembly. Such an embodiment is shown in FIGS. 8A and 8B. In accordance with this aspect of the invention, the catheter 10 carries a coolant injection tube 1 which extends to a cooling chamber structure 103 that is surrounded by a cooling balloon 112. The cooling chamber structure 103 is relatively stiff or even rigid and has substantially fixed dimensions. It may be implemented, for example with a cylinder formed of hard polymer or metal and having a fixed diameter. Surrounding the cooling chamber cylinder 103 is a balloon 112 shown in its deflated state in FIG. 8A and shown fully inflated in FIG. 8B. When the cooling and balloon inflation are carried out by the same medium, the cooling chamber 103 may be implemented with a perforated chamber wall. The use of a substantially rigid chamber 103 allows the coolant flow upon exiting the injection tube to undergo substantially regular conditions and therefore provides well regulated and predictable cooling characteristics. However, the invention also contemplates that the balloon may be inflated with a pressurizing medium other than that provided by the refrigerant. In either case the balloon may be formed of a quite thin membrane, on the order of 0.02 millimeters thickness or less, so that in this case it presents very little impediment to heat conduction.

In this construction, the balloon serves as a compliance member to conform to irregular tissue surfaces, and may be used to apply pressure to a lumen to enlarge the lumen in a manner similar to that employed in coronary angioplasty and fallopian tuboplasty procedures. The balloon may also be operated to occlude blood flow when used in an endovascular catheter for rapid therapy since the inflation portion may be deployed or deflated substantially instantaneously. The balloon further operates to center the cooling chamber within the lumen, thus assuring substantially concentric cooling characteristics for the treatment. Finally, the balloon serves to anchor the cooling chamber in position.

The provision of a fixed dimension cooling chamber surrounded by an annular balloon that is inflated by a separate medium, advantageously provides an enhanced spectrum of operating characteristics. Several examples follow illustrating the range of this construction of the invention.

FIGS. 9A and 9B schematically illustrate the construction of a guide wire cryocatheter 200 having such a circumferential cushioning balloon 212. This construction may also be applied to cooling other cylindrical tissue structures or body lumens, including organs or structures such as the fallopian tube, esophagus, biliary duct, ureter, gastrointestinal tract and the bronchus. For each of these different applications, the relative diameter of the cooling chamber and the thickness of balloon portion may be varied so as to achieve for example high total cooling with a large cooling chamber and an effective rate of heat transfer from the surrounding tissue area through a relatively thinner layer of cooling balloon. Notably, the balloon may inflated with a medium such as precooled saline solution having a high rate of thermal conductivity and a high thermal storage capacity, to achieve quick chilling and to maintain a stable thermal set point without having to design the cooling chamber to bear the full thermal load alone.

As shown in FIG. 9A, the injection tube 201 enters the expansion chamber 203 and injects refrigerant at high pressure, which then expands in the chamber and is exhausted through the exhaust lumen 205 which constitutes the major portion of the catheter shaft. The balloon 212, shown in its collapsed state in FIG. 9A around the circumference of the cooling chamber, is inflated via a balloon inflation lumen 208. Applicant contemplates that the balloon inflation may be effected by a number of inflation media, including a gaseous coolant medium from the other (coolant) chamber 203. However, preferably, in this embodiment an incompressible liquid such as saline solution having a high thermal capacity and excellent heat conductive properties is applied through the inflation tube 208 to fill the balloon as shown in FIG. 9B. The external surface of the expansion chamber 203 may be provided with texture, such as a plurality of isolated bumps or dimples 207, of which several are shown in cross-section, to provide unobstructed fluid percolation passages along the surface and assure that the balloon inflation fluid may have free access and flow quickly to and from the passage 208. This allows the balloon to fully deflate when fluid is withdrawn via passage 208.

A guide wire lumen 220 passes centrally through the cooling chamber assembly and as shown in FIG. 9B accommodates a guide wire 221 for directing and positioning the catheter. As further shown in those Figures, the outer diameter of the cooling chamber may extend for a relatively great portion of the total diameter of the device so that the balloon portion occupies only a thin shell which effectively extends the reach of the cooling chamber and provides a short heat conduction path together with firm compliant contact with surrounding tissue. As noted above, when used for angioplasty and other cryogenic treatment contexts the balloon serves to apply a stretching or extensile force to tissue, which is conducive to the desired tissue treatment destruction or regeneration process. The provision of such enlarged cooling chamber also provides a greater external surface area for the coldest central structure of the catheter, greatly enhancing the rate of thermal transfer achieved with the balloon assembly.

In general the body of the catheter may be comparable to that of existing treatment devices, e.g., one to four centimeters in length for an endovascular angioplasty device. However the cryogenic portion need not extend the full length of the tip assembly, and the structure may include axial extension portions which are not cryogenically cooled.

Figure 10A:
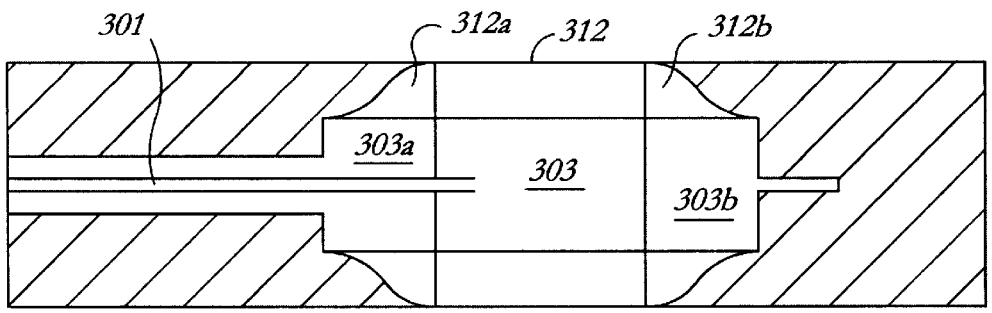
FIGS. 10A–10B show yet another balloon embodiment.
Figure 10B:
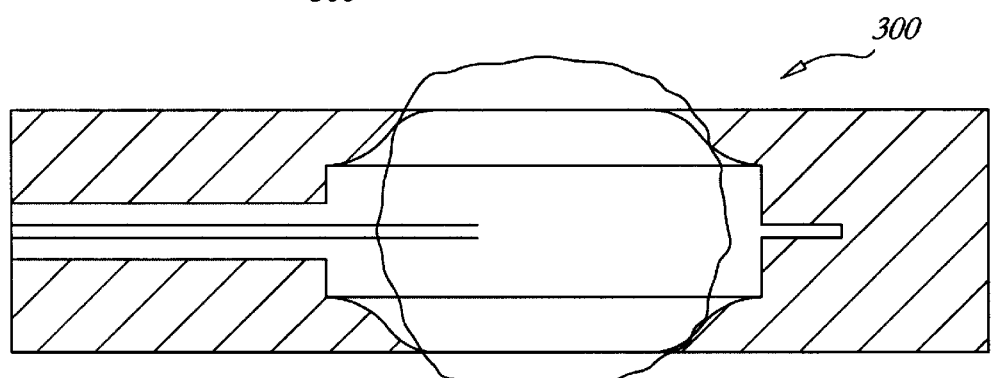
Figure 10C:
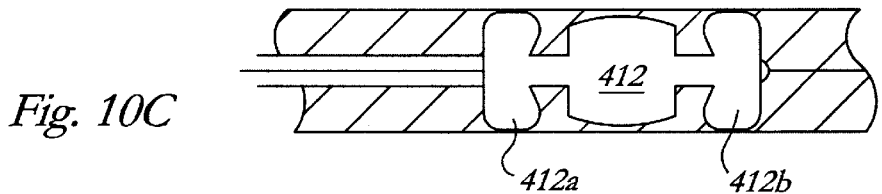
FIG. 10C illustrates a further variation on the embodiment of FIGS. 10A–10B.

FIGS. 10A through 10C illustrate a construction of a cryocatheter 300 of this type. In this embodiment, the tip of the catheter includes chambers 303, 303a and 303b all located within the balloon. The chamber 303 serves as a cooling expansion chamber in the manner described above, and the cooling injection tube 301 opens into that chamber. At the proximal and distal ends of chamber 303, pair of dummy chambers 303a, 303b extend continuously with the main body of the chamber to form a single elongated cylindrical structure lying within the balloon 312. However, the end chambers 303a, 303b are isolated from the injected coolant, and themselves form dummy spaces or uncooled regions that serve simply to provide positioning support. As further shown in FIG. 10A, the balloon 312 has corresponding segments denoted 312a, 312b and 312c that are partitioned from each other such that the end segments are separated from the central cooling portion of the balloon. These segments lie over subchambers 303a, 303 and 303b. They may be serially connected or separately supplied with inflation material, so fluid entering the balloons is cooled only in the central region.

The illustrated embodiment of FIG. 10A has a generally continuous balloon contour in which at least a portion of the end segments 312a, 312b inflates to the diameter of the surrounding blood vessel or tissue lumen and serves to displace blood, fluid or tissue away from the cryogenic treatment portion at the center of the catheter tip. As shown in FIG. 10B, this has the effect of creating a cooling region that forms a relatively symmetrical ice ball volume (indicated by dashed lines in the FIG.) around the vessel and catheter tip, with greater depth of penetration centered directly over the cryogenic chamber and with cooling damage tapering off away from that region. The balloon need not be a single continuous or partitioned balloon but may be implemented with separate balloons that in turn may be inflated via separate filler or inflation tubes (not illustrated) so as to more effectively achieve or more independently initiate the blocking and heat isolation functions. FIG. 10C illustrates one such embodiment 400, in which a cryogenic balloon 412 is surrounded by first and second blocking or blood displacing balloons 412a, 412b that are offset a short distance away from the ends of the coolant chamber. With this construction the excluding balloons may be positioned more remotely from the cryogenic segment.

In any of the foregoing embodiments, the balloon may be configured to apply a chilling level of cold without freezing or destroying tissue when appropriate for the tissue involved. As with the basic embodiment shown in FIGS. 8A and 8B, the catheter of the present invention preferably allows the withdrawal of sufficient thermal energy form the target site to freeze tissue, while the balloon anchors or enhances the positioning of the cryogenic source within the lumen so as to deploy the resulting ice ball in an appropriate relation to the surrounding tissue. The balloon enhances control of adjacent blood flow and may be used to arrest blood flow in the vessel entirely so that therapeutic cold accrues more quickly and is not dissipated. By actively pumping out the inflation fluid, collapse of the balloon following therapy allows more immediate resumption of circulation to perfuse tissue. Furthermore, by using a liquid-inflated balloon, the device may be deployed in much the same manner as an existing angioplasty catheter, and the guide wire lumen allows simple navigation and use of the device without requiring that the physician or cardiology specialist acquire additional operating skills or specialized training.

The catheter shaft may accommodate various lumens either as part of the shaft extrusion, or by carrying them as separate tubes such as an injection tube, a coolant exhaust lumen, a balloon inflation lumen, a guide wire lumen and other lumens, for example, for carrying wires to heating elements and/or monitoring devices to sense pressure, temperature and other sensing functions. By making the diameter of the cryogenic chamber large in relation to the targeted tissue lumen, the balloon may be formed with a low interior volume, facilitating the thawing of the inflation medium and reducing the time of total vascular obstruction. The thawing may further be advanced by providing and activating one or more heating elements, which may include any of a wide variety of heating means within the catheter body, such as resistive heating, radio frequency heating, laser heating applied via an optical fiber extending through the catheter body, microwave heating or heated gas or liquid infusion applied to the balloon portion. These may also include, in various treatment regimens, sources of energy that are externally applied to a catheter designed to preferentially receive such energy. Such external heating energy sources may, for example, be ultrasound or electromagnetic radiation applicators. The heater may also include various semiconductor, thin layer resistive or other similar technologies deployed, for example, on the balloon surface so as to heat one or more of the wall of the body lumen, the balloon inflation medium, or various pieces of the catheter structure.

Figure 11:
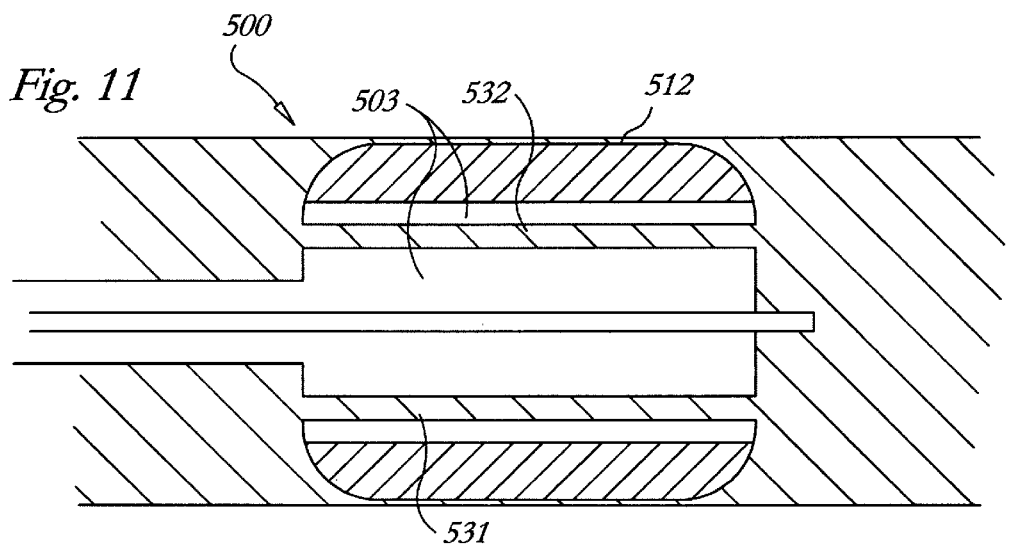
FIG. 11 illustrates another embodiment.

In addition, the period of blood flow obstruction may be further reduced by providing a structure as shown in FIG. 11. In this case, the catheter 500 includes perfusion channels 531, 532 that extend through the catheter structure to allow blood to flow along the tissue lumen during the balloon inflation time interval and before extreme cooling has occurred to freeze off the central region. In this embodiment, the balloon may be inflated to securely position and center the assembly while blood continues to flow along the vessel. Cooling is then started. While the bypass channels 531, 532 may be expected to freeze off once the cooling injection has started, the invention also contemplates that the bypass channels may be insulated from the cooling chamber, or they may include resistive or other heating elements to maintain their temperature suitable for continued blood flow during cryoablation. Such bypass passages may also be positioned in part in or through the catheter shaft or guide wire lumen.

The invention also contemplates a catheter as described above combined with other known catheter subassemblies or accessory devices such as drug delivery, energy delivery or stent delivery elements, or structures for delivering radiation. In other embodiments the catheter may include one or more additional balloons such as a primary angioplasty balloon in addition to the blocking balloons and the cryotreatment balloon described above. In yet other embodiments of the invention, the catheter may include a supply tube for ejecting a bioactive or simply thermally conductive material in the space surrounding the cooling portion, to form a temporary frozen plug which may be left in place following withdrawal of the catheter.

Figure 12B:
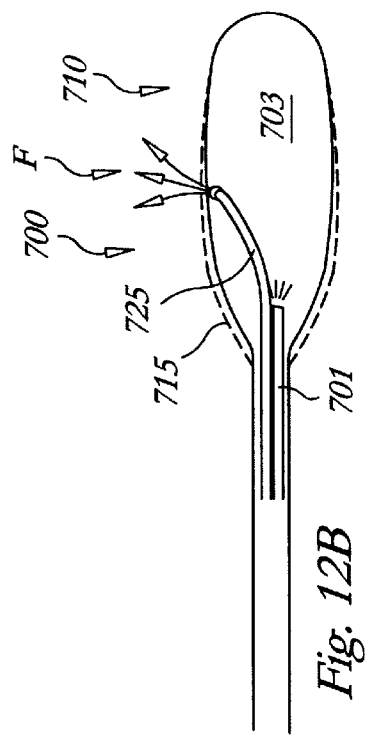
FIGS. 12A and 12B illustrate delivery embodiments.
Figure 12A:
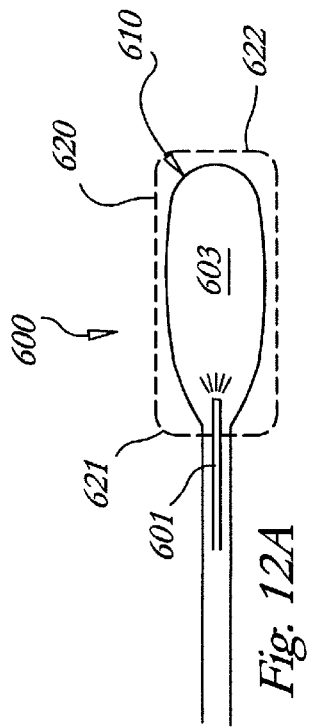

FIGS. 12A and 12B illustrate two such delivery catheters 600, 700. As shown in FIG. 12A, a first delivery catheter 600 includes an elongated body and cryogenic tip 610 with a cooling chamber 603 fed by a coolant injection lumen 601 as described above. Catheter 600 further carries a stent 620 on its outer surface and is configured to deliver and install the stent at an endoluminal site. By way of example the stent 620 is illustrated as having ends 621, 622 contoured to retain the stent on the catheter during delivery, but other retention means, such as a removable or telescoping retaining sheath may be employed. The stent is made of a shape-memory alloy or other biphasic temperature-dependent material that changes its shape when brought to predetermined temperature. For operation, the catheter tip is deployed to a desired site and then operated to bring about a temperature-dependent change in shape or dimension of the stent 620. This may be accomplished before, during, after, or independently of, the cryogenic treatment of nearby tissue. Depending on the particular alloy employed in stent 620, the fixation in position and shape change may be effected by applying cryogenic temperature, or else a mild amount of cooling may be applied to cause the stent to retain a compact shape during insertion and the stent may subsequently deploy as the surrounding temperature rises to normal body temperature. It will be understood that in general the alloy properties of such materials may be adjusted so that a relatively large change in shape or conformation is achieved at one temperature threshold, which may be above or below body temperature. Accordingly, for this aspect of the invention, applicant contemplates the possibility of providing a heater as well as the cryochamber 603 to provide both hypo- and hyperthermal conditions to carry out stent deployment.

FIG. 12B illustrates another embodiment 700 of a cryogenic delivery catheter of the invention. This embodiment again has the basic structure of a cooling chamber 703 in a distal cooling tip 710 fed by a coolant supply lumen 701. However, in this embodiment an additional fluid delivery line 725 extends through the catheter body and is mounted to deliver fluid F externally of the tip 710 into the space between the cooling chamber exterior wall and the surrounding tissue. The delivery line 725 may have one or more outlets positioned to provide fluid F in defined locations. As illustrated in phantom by element 715, a perforated membrane or other external distribution structure may also be provided to disperse or spread the fluid F exiting the delivery line 725. In general, the delivery line 725 may deliver a therapeutic treatment liquid, or simply a heat conduction fluid to cryochamber surface. Applicant contemplates generally that during cryotreatment, the fluid F will freeze in place, forming a plug that blocks flow, conducts thermal energy, and otherwise cooperates with the cryotreatment operation as described above. Advantageously, however, upon ( or even prior to) completion of the freezing treatment, the catheter 700 may be withdrawn while leaving the frozen fluid mass in place. This mass then continues to chill the lumenal tissue wall, while (in the case of a vessel) circulation is immediately restored through the center. Thus, the duration of catheter freezing operation or the duration of blood flow occlusion may each be reduced, offering significant clinical advantages.

The foregoing describes several embodiments of the invention and preferred implementations thereof. It will be understood that the foregoing catheter constructions permit inclusion of many features commonly appearing in known catheter or catheter-like devices, such as a guide wire lumen, a sampling lumen, or a lumen and related fluid delivery structure for operation as a perfusion catheter. The invention being thus disclosed and described, further variations and modifications will occur to those skilled in the art, and all such variations and modifications are intended to be within the scope of the present invention, as defined by the claims appended hereto and equivalents thereof.

What is claimed is:

1. A catheter for endovascular cryotreatment of tissue, comprising:
   a handle,
   an elongated catheter body having:
      a proximal end portion, the proximal end portion being coupled to the handle,
      a distal end portion,
      an injection tube, the injection tube being coupled to a supply of coolant fluid, and
      a return passage, the return passage being coupled to the handle, the return passage having a controllable back pressure regulated by the handle, and
   at least one balloon positioned at the distal end portion of the elongated catheter body, the at least one balloon being configured for inflation by the supply of coolant fluid such that the balloon expands within a vessel to occlude the vessel and position the balloon wall in thermal contact with the vessel wall for effecting cryotreatment, the at least one balloon having at least one metallized surface region of enhanced thermal conductivity to selectively freeze the vessel wall in proximity to said surface region.

2. A cryocatheter assembly in accordance with claim 1, wherein the at least one metallized surface region is patterned.

3. A cryocatheter assembly in accordance with claim 2, wherein the at least one metallized surface region has a pattern configured for radial expansion without stress cracking.

4. A cryocatheter assembly in accordance with claim 2, wherein the at least one metallized surface region has a pattern including an array of separated heat conduction regions.

5. A cryocatheter assembly in accordance with claim 2, wherein said pattern is a discrete pattern effective for ablation treatment of the vascular wall.

6. A catheter for endovascular cryotreatment of tissue, comprising:

a handle coupled to a supply of cooling fluid, and an elongated catheter body having a proximal end and a distal end, the proximal end being coupled to the handle, the distal end further comprising:
- a cooling segment, the cooling segment having a fluid impermeable heat exchanging surface, and
- at least one balloon positioned proximate the cooling segment, wherein the cooling segment is cooled by the flow of cooling fluid, and the at least one balloon is configured for inflation by said cooling fluid, the elongated catheter body and handle further forming a return passage for said fluid wherein the return passage is set with a back pressure effective for inflating the balloon with the cooling fluid such that the balloon expands within a vessel to occlude the vessel while the cooling segment is positioned in thermal contact proximate the vessel wall for performing cryotreatment.

7. A cryocatheter assembly in accordance with claim 6, wherein the at least one balloon comprises a membrane having a surface region of tapered aspect for lodging in a vessel ostium.

8. A cryocatheter assembly in accordance with claim 6, wherein the catheter is configured for trickle inflation of the at least one balloon with the flow of cooling fluid from the cooling segment.

9. A cryocatheter assembly in accordance with claim 6, wherein the at least one balloon inflates with cooling fluid to provide a supplemental region of ice formation at the surface of the balloon.

10. A cryocatheter assembly in accordance with claim 6, wherein, relative to the handle, the at least one balloon is positioned distal to the cooling segment.

11. A cryocatheter assembly in accordance with claim 6, wherein, relative to the handle, the at least one balloon is positioned proximal to the cooling segment.

12. A cryocatheter assembly in accordance with claim 6, wherein at least one balloon is a primary balloon, and further comprising a shaped balloon conformable to a vessel ostium, and wherein the cooling segment lies between the primary balloon and the shaped balloon.

13. A cryocatheter comprising:
- an elongated catheter body having a proximal end portion and a distal end portion,
- a handle coupled to the proximal end portion, the handle being in fluid communication with a supply of coolant,
- a substantially rigid cooling chamber positioned at the distal end portion,
- said catheter body being configured for insertion in a tissue lumen, and including a coolant injection lumen for carrying coolant to said cooling chamber and a return lumen for return of coolant, and
- an inflatable sleeve mounted about said cooling chamber, said sleeve being inflatable through said catheter body with a heat conductive inflation medium to form a compliant contact with surrounding tissue and effect thermal conduction between said tissue and the cooling chamber.

14. The cryocatheter of claim 13, wherein said sleeve is a balloon, and said ballon is further configured to perform at least one of the functions of
   i) anchoring and positioning the cooling chamber;
   ii) blocking blood flow past the cooling chamber; and p1
   iii) exerting expansive force on adjacent tissue.

15. A cryocatheter comprising a handle an elongated catheter body extending from the handle to a cooling chamber, said catheter body being configured for insertion in a tissue lumen, and including a coolant injection lumen for carrying coolant to said cooling chamber and a return lumen for return of coolant, and an inflatable sleeve mounted about said cooling chamber, said sleeve being inflatable through said catheter body with a heat conductive inflation medium to form a compliant contact with surrounding tissue and effect thermal conduction between said tissue and the cooling chamber; said inflatable sleeve and cooling chamber constituting a tissue cooling assembly, and further comprising a bypass passage extending through the tissue cooling assembly to allow fluid flow along the tissue lumen while said assembly is positioned in the tissue lumen and the sleeve is inflated.

16. The cryocatheter of claim 15, further comprising heating means for rewarming at least one of the inflation medium, a distal portion of the catheter, and the surrounding tissue.

17. The cryocatheter of claim 15 wherein the catheter is a perfusion catheter.

* * * * *

UNITED STATES PATENT AND TRADEMARK OFFICE
CERTIFICATE OF CORRECTION

PATENT NO. : 6,283,959 B1
DATED : September 4, 2001
INVENTOR(S) : Jean Pierre Lalonde et al.

It is certified that error appears in the above-identified patent and that said Letters Patent is hereby corrected as shown below:

<u>Column 16,</u>
Line 18, delete "p1"

Signed and Sealed this

Ninth Day of September, 2003

JAMES E. ROGAN
*Director of the United States Patent and Trademark Office*